US012685449B2

(12) United States Patent
Bechtel et al.

(10) Patent No.: US 12,685,449 B2
(45) Date of Patent: Jul. 21, 2026

(54) SYSTEM AND METHOD FOR MEASURING BLOOD PRESSURE

(71) Applicant: ROCKLEY PHOTONICS LIMITED, Altrincham (GB)

(72) Inventors: Kate LeeAnn Bechtel, Pleasant Hill, CA (US); Mohsen Naji, Mission Viejo, CA (US)

(73) Assignee: Rockley Photonics Limited, Altrinchman (GB)

( * ) Notice: Subject to any disclaimer, the term of this patent is extended or adjusted under 35 U.S.C. 154(b) by 0 days.

(21) Appl. No.: 18/778,893

(22) Filed: Jul. 19, 2024

(65) Prior Publication Data

US 2025/0025058 A1      Jan. 23, 2025

Related U.S. Application Data

(60) Provisional application No. 63/514,994, filed on Jul. 21, 2023.

(51) Int. Cl.
| | |
|---|---|
| *A61B 5/021* | (2006.01) |
| *A61B 5/00* | (2006.01) |
| *A61B 5/022* | (2006.01) |
| *A61B 5/0295* | (2006.01) |

(52) U.S. Cl.
CPC ...... *A61B 5/02116* (2013.01); *A61B 5/02141* (2013.01); *A61B 5/02208* (2013.01); *A61B 5/0295* (2013.01); *A61B 5/7221* (2013.01); *A61B 5/7246* (2013.01); *A61B 5/7275* (2013.01); *A61B 2562/0247* (2013.01)

(58) Field of Classification Search
None
See application file for complete search history.

(56)      References Cited

U.S. PATENT DOCUMENTS

| | | | |
|---|---|---|---|
| 4,674,011 | A | 6/1987 | Patton et al. |
| 5,243,983 | A | 9/1993 | Tarr et al. |
| 5,497,769 | A | 3/1996 | Gratton et al. |
| 5,532,860 | A | 7/1996 | Hershey et al. |
| | | (Continued) | |

FOREIGN PATENT DOCUMENTS

| | | |
|---|---|---|
| CA | 2 861 089 C | 1/2021 |
| CN | 108709847 A | 10/2018 |
| | (Continued) | |

OTHER PUBLICATIONS

Ghijsen et al; Wearable speckle plethysmography (SPG) for characterizing microvascular flow and resistance; vol. 9, No. 8 | Aug. 1, 2018 | Biomedical Optics Express 3937 (Year: 2018).*

(Continued)

*Primary Examiner* — Jay B Shah

(74) *Attorney, Agent, or Firm* — Womble Bond Dickinson (US) LLP

(57)      ABSTRACT

A system and method for measuring blood pressure. In some embodiments, a system includes a speckleplethysmography sensor and a processing circuit. The system may be configured: to perform, using the speckleplethysmography sensor, blood flow measurements of a subject, and measurements of cuff pressure of a cuff worn by the subject, while the cuff pressure varies; and to calculate, from the blood flow measurements and the cuff pressure measurements, a first blood pressure.

6 Claims, 6 Drawing Sheets

(56) References Cited

U.S. PATENT DOCUMENTS

| | | | |
|---|---|---|---|
| 5,772,587 | A | 6/1998 | Gratton et al. |
| 5,830,132 | A | 11/1998 | Robinson |
| 6,154,259 | A | 11/2000 | Hargis et al. |
| 6,243,601 | B1 | 6/2001 | Wist |
| 6,246,892 | B1 | 6/2001 | Chance |
| 6,256,016 | B1 | 7/2001 | Piot et al. |
| 6,560,478 | B1 | 5/2003 | Alfano et al. |
| 6,919,549 | B2 | 7/2005 | Bamji et al. |
| 7,035,679 | B2 | 4/2006 | Addison et al. |
| 7,113,817 | B1 | 9/2006 | Winchester, Jr. et al. |
| 7,202,466 | B2 | 4/2007 | Babayoff et al. |
| 7,250,317 | B2 | 7/2007 | Heideman |
| 7,295,783 | B2 | 11/2007 | Singh et al. |
| 7,375,812 | B2 | 5/2008 | Atia et al. |
| 7,474,407 | B2 | 1/2009 | Gutin |
| 7,505,128 | B2 | 3/2009 | Zribi et al. |
| 7,616,984 | B2 | 11/2009 | Barbour et al. |
| 7,761,126 | B2 | 7/2010 | Gardner et al. |
| 7,865,225 | B2 | 1/2011 | Kaltschmidt et al. |
| 7,922,664 | B2 | 4/2011 | Elliott |
| 7,925,056 | B2 | 4/2011 | Presura et al. |
| 8,237,927 | B1 | 8/2012 | Reeve et al. |
| 8,277,384 | B2 | 10/2012 | Fine |
| 8,313,439 | B2 | 11/2012 | Mccombie et al. |
| 8,343,062 | B2 | 1/2013 | Fortin et al. |
| 8,343,063 | B2 | 1/2013 | Borgos |
| 8,376,955 | B2 | 2/2013 | Baker, Jr. |
| 8,398,556 | B2 | 3/2013 | Sethi et al. |
| 8,868,149 | B2 | 10/2014 | Eisen et al. |
| 8,920,332 | B2 | 12/2014 | Hong et al. |
| 8,923,942 | B2 | 12/2014 | Bernreuter |
| 8,945,017 | B2 | 2/2015 | Venkatraman et al. |
| 8,948,832 | B2 | 2/2015 | Hong et al. |
| 8,956,303 | B2 | 2/2015 | Hong et al. |
| 8,998,815 | B2 | 4/2015 | Venkatraman et al. |
| 9,005,129 | B2 | 4/2015 | Venkatraman et al. |
| 9,113,794 | B2 | 8/2015 | Hong et al. |
| 9,113,795 | B2 | 8/2015 | Hong et al. |
| 9,149,216 | B1 | 10/2015 | Eisen et al. |
| 9,155,480 | B2 | 10/2015 | Thaker et al. |
| 9,226,673 | B2 | 1/2016 | Ferguson, Jr. et al. |
| 9,237,855 | B2 | 1/2016 | Hong et al. |
| 9,307,917 | B2 | 4/2016 | Hong et al. |
| 9,494,567 | B2 | 11/2016 | Islam |
| 9,687,162 | B2 | 6/2017 | Vetter et al. |
| 9,704,050 | B2 | 7/2017 | Lee et al. |
| 9,730,622 | B2 | 8/2017 | Eisen et al. |
| 9,772,280 | B2 | 9/2017 | Cerussi et al. |
| 9,804,027 | B2 | 10/2017 | Fish et al. |
| 9,846,126 | B2 | 12/2017 | Gunn, III et al. |
| 9,848,787 | B2 | 12/2017 | White et al. |
| 9,851,298 | B1 | 12/2017 | Isikman et al. |
| 9,877,681 | B2 | 1/2018 | Silverman |
| 9,931,040 | B2 | 4/2018 | Homyk et al. |
| 9,970,955 | B1 | 5/2018 | Homyk et al. |
| 10,004,406 | B2 | 6/2018 | Yuen et al. |
| 10,058,256 | B2 | 8/2018 | Chen et al. |
| 10,178,959 | B1 | 1/2019 | Homyk et al. |
| 10,178,973 | B2 | 1/2019 | Venkatraman et al. |
| 10,194,808 | B1 | 2/2019 | Thompson et al. |
| 10,206,576 | B2 | 2/2019 | Shcherbakov et al. |
| 10,215,698 | B2 | 2/2019 | Han et al. |
| 10,241,033 | B2 | 3/2019 | Uematsu et al. |
| 10,271,740 | B2 | 4/2019 | Ward et al. |
| 10,314,532 | B2 | 6/2019 | Ward et al. |
| 10,326,035 | B2 | 6/2019 | Lu et al. |
| 10,326,036 | B2 | 6/2019 | Sweeney et al. |
| 10,349,847 | B2 | 7/2019 | Kwon et al. |
| 10,352,768 | B2 | 7/2019 | Simpkin et al. |
| 10,357,165 | B2 | 7/2019 | Yoon |
| 10,420,498 | B1 | 9/2019 | Horstmeyer et al. |
| 10,422,693 | B2 | 9/2019 | Fish et al. |
| 10,451,537 | B2 | 10/2019 | Nakaji |
| 10,463,286 | B2 | 11/2019 | Schenkman et al. |
| 10,492,684 | B2 | 12/2019 | Khachaturian et al. |
| 10,506,926 | B2 | 12/2019 | Khachaturian et al. |
| 10,506,955 | B2 | 12/2019 | Thell et al. |
| 10,568,527 | B2 | 2/2020 | Yoon et al. |
| 10,588,519 | B2 | 3/2020 | Yuen et al. |
| 10,602,987 | B2 | 3/2020 | Khachaturian et al. |
| 10,627,849 | B1 | 4/2020 | Scofield et al. |
| 10,641,962 | B2 | 5/2020 | Nykanen et al. |
| 10,643,903 | B2 | 5/2020 | Drake et al. |
| 10,667,688 | B2 | 6/2020 | Khachaturian et al. |
| 10,677,989 | B2 | 6/2020 | Abediasl et al. |
| 10,681,259 | B2 | 6/2020 | Ichiki et al. |
| 10,681,283 | B2 | 6/2020 | Nakashima et al. |
| 10,694,997 | B2 | 6/2020 | Kim et al. |
| 10,718,668 | B2 | 7/2020 | Gu et al. |
| 10,722,177 | B2 | 7/2020 | Homyk et al. |
| 10,739,256 | B1 | 8/2020 | Rickman et al. |
| 10,750,956 | B2 | 8/2020 | Zalevsky et al. |
| 10,775,239 | B2 | 9/2020 | Lee et al. |
| 10,813,597 | B2 | 10/2020 | Rice et al. |
| 10,820,858 | B2 | 11/2020 | Yoon et al. |
| 10,842,422 | B2 | 11/2020 | Yu et al. |
| 10,871,503 | B1 | 12/2020 | Homyk et al. |
| 10,895,525 | B2 | 1/2021 | Swanson |
| 10,966,616 | B2 | 4/2021 | De Morree et al. |
| 10,973,422 | B2 | 4/2021 | Pantelopoulos et al. |
| 11,022,751 | B2 | 6/2021 | Bauters et al. |
| 11,045,103 | B2 | 6/2021 | Shchekin et al. |
| 11,079,364 | B2 | 8/2021 | Leger et al. |
| 11,096,601 | B2 | 8/2021 | Hong et al. |
| 11,096,608 | B2 | 8/2021 | Van Dorpe et al. |
| 11,129,544 | B2 | 9/2021 | Zalevsky et al. |
| 11,202,582 | B2 | 12/2021 | Verkruijsse et al. |
| 11,213,217 | B2 | 1/2022 | Han et al. |
| 11,278,220 | B2 | 3/2022 | Tucker et al. |
| 11,298,035 | B2 | 4/2022 | Huijbregts et al. |
| 11,369,275 | B2 | 6/2022 | Song et al. |
| 11,445,922 | B2 | 9/2022 | Naima |
| 11,553,851 | B2 | 1/2023 | Kim et al. |
| 11,583,185 | B2 | 2/2023 | Homyk et al. |
| 11,666,238 | B2 | 6/2023 | Rege et al. |
| 11,666,277 | B2 | 6/2023 | Yoon et al. |
| 11,684,281 | B2 | 6/2023 | Pantelopoulos et al. |
| 11,690,513 | B2 | 7/2023 | Hu et al. |
| 11,696,693 | B2 | 7/2023 | Wong |
| 11,709,120 | B2 | 7/2023 | Rice et al. |
| 11,744,491 | B2 | 9/2023 | Dunn et al. |
| 11,751,811 | B2 | 9/2023 | Sun et al. |
| 11,759,116 | B2 | 9/2023 | White et al. |
| 11,759,121 | B2 | 9/2023 | Mccann et al. |
| 11,771,343 | B2 | 10/2023 | Sacha |
| 11,800,990 | B2 | 10/2023 | White et al. |
| 11,857,301 | B1 | 1/2024 | Homyk et al. |
| 11,883,134 | B2 | 1/2024 | Leabman |
| 11,890,081 | B2 | 2/2024 | Jang |
| 11,980,451 | B2 | 5/2024 | Albert |
| 12,109,006 | B2 | 10/2024 | Dunn et al. |
| 12,193,800 | B2 | 1/2025 | Bechtel et al. |
| 12,201,396 | B2 | 1/2025 | Dunn et al. |
| 12,396,648 | B1 | 8/2025 | McMillan |
| 2002/0068859 | A1 | 6/2002 | Knopp |
| 2002/0195496 | A1 | 12/2002 | Tsikos et al. |
| 2003/0052169 | A1 | 3/2003 | Tsikos et al. |
| 2003/0137669 | A1 | 7/2003 | Rollins et al. |
| 2005/0249509 | A1 | 11/2005 | Nagarajan et al. |
| 2006/0124829 | A1 | 6/2006 | Song et al. |
| 2006/0132790 | A1 | 6/2006 | Gutin |
| 2006/0204175 | A1 | 9/2006 | Laurent-Lund et al. |
| 2006/0247514 | A1 | 11/2006 | Panasyuk et al. |
| 2007/0051601 | A1 | 3/2007 | Wang et al. |
| 2007/0057182 | A1 | 3/2007 | Feuerbaum |
| 2007/0093702 | A1 | 4/2007 | Yu et al. |
| 2008/0097172 | A1 | 4/2008 | Sawada et al. |
| 2008/0154126 | A1 | 6/2008 | Culver et al. |
| 2008/0204752 | A1 | 8/2008 | Dorvee et al. |
| 2008/0220512 | A1 | 9/2008 | Koh et al. |
| 2008/0316567 | A1 | 12/2008 | Grasser et al. |
| 2009/0177094 | A1 | 7/2009 | Brown et al. |
| 2009/0202251 | A1 | 8/2009 | Shibayama |

(56) References Cited

U.S. PATENT DOCUMENTS

| | | |
|---|---|---|
| 2009/0209834 A1* | 8/2009 | Fine .................... A61B 5/0261 |
| | | 600/479 |
| 2009/0284748 A1 | 11/2009 | Melman et al. |
| 2010/0004741 A1 | 1/2010 | Gupta et al. |
| 2010/0046234 A1 | 2/2010 | Abu-Ageel |
| 2010/0056928 A1 | 3/2010 | Zuzak et al. |
| 2010/0226646 A1 | 9/2010 | Chan et al. |
| 2011/0054277 A1 | 3/2011 | Pinter et al. |
| 2011/0082355 A1 | 4/2011 | Eisen et al. |
| 2011/0087108 A1 | 4/2011 | Onoe et al. |
| 2011/0196244 A1 | 8/2011 | Ribas Ripoll et al. |
| 2012/0130215 A1 | 5/2012 | Fine et al. |
| 2012/0232402 A1 | 9/2012 | MacFarlane et al. |
| 2013/0131475 A1 | 5/2013 | Eisen et al. |
| 2013/0190630 A1 | 7/2013 | Borgos |
| 2013/0204112 A1 | 8/2013 | White et al. |
| 2013/0278631 A1 | 10/2013 | Border et al. |
| 2014/0094666 A1 | 4/2014 | Fine |
| 2014/0118695 A1 | 5/2014 | Shimada et al. |
| 2014/0120319 A1 | 5/2014 | Joseph |
| 2014/0200423 A1 | 7/2014 | Eisen et al. |
| 2014/0313524 A1 | 10/2014 | Banyay et al. |
| 2014/0316286 A1 | 10/2014 | Addison et al. |
| 2014/0376001 A1 | 12/2014 | Swanson |
| 2015/0157224 A1 | 6/2015 | Carmon et al. |
| 2015/0196251 A1 | 7/2015 | Outwater et al. |
| 2015/0201854 A1 | 7/2015 | Hong et al. |
| 2015/0323311 A1 | 11/2015 | Muijs et al. |
| 2016/0058300 A1 | 3/2016 | Yoon et al. |
| 2016/0066790 A1 | 3/2016 | Shcherbakov et al. |
| 2016/0106327 A1 | 4/2016 | Yoon et al. |
| 2016/0157736 A1 | 6/2016 | Huang et al. |
| 2016/0161685 A1 | 6/2016 | Xu et al. |
| 2016/0183882 A1 | 6/2016 | Henley et al. |
| 2016/0195473 A1 | 7/2016 | Fujiwara et al. |
| 2016/0242647 A1 | 8/2016 | Ishii et al. |
| 2016/0266337 A1 | 9/2016 | Feng |
| 2016/0278676 A1 | 9/2016 | Eisen et al. |
| 2016/0282265 A1 | 9/2016 | Su et al. |
| 2016/0287107 A1 | 10/2016 | Szabados et al. |
| 2016/0360966 A1 | 12/2016 | Ishii et al. |
| 2017/0007138 A1 | 1/2017 | Kim et al. |
| 2017/0014037 A1 | 1/2017 | Coppola et al. |
| 2017/0065184 A1 | 3/2017 | Barak |
| 2017/0105618 A1 | 4/2017 | Schmoll et al. |
| 2017/0108439 A1 | 4/2017 | Stievater et al. |
| 2017/0138789 A1 | 5/2017 | Ivanov |
| 2017/0164878 A1 | 6/2017 | Connor |
| 2017/0188851 A1 | 7/2017 | LeBoeuf et al. |
| 2017/0231513 A1 | 8/2017 | Presura et al. |
| 2017/0315292 A1 | 11/2017 | Mullen et al. |
| 2018/0020962 A1 | 1/2018 | Yu et al. |
| 2018/0045566 A1 | 2/2018 | Fish et al. |
| 2018/0064399 A1 | 3/2018 | Buettgen et al. |
| 2018/0110423 A1 | 4/2018 | Presura et al. |
| 2018/0160913 A1 | 6/2018 | Fine |
| 2018/0168465 A1 | 6/2018 | Yamada et al. |
| 2018/0202927 A1 | 7/2018 | Isikman et al. |
| 2018/0228363 A1 | 8/2018 | Frisken et al. |
| 2018/0238794 A1 | 8/2018 | Kangas et al. |
| 2018/0263519 A1 | 9/2018 | Gu |
| 2018/0283950 A1 | 10/2018 | Ge et al. |
| 2018/0296168 A1 | 10/2018 | Rice et al. |
| 2019/0005351 A1 | 1/2019 | Zhou et al. |
| 2019/0041736 A1 | 2/2019 | Grunnet-Jepsen et al. |
| 2019/0046056 A1 | 2/2019 | Khachaturian et al. |
| 2019/0053721 A1 | 2/2019 | Boas et al. |
| 2019/0094009 A1 | 3/2019 | Aizawa et al. |
| 2019/0094564 A1 | 3/2019 | Rivera et al. |
| 2019/0167118 A1 | 6/2019 | Vilenskii et al. |
| 2019/0175030 A1 | 6/2019 | Verkruijsse et al. |
| 2019/0336006 A1 | 11/2019 | Horstmeyer et al. |
| 2019/0343442 A1 | 11/2019 | Aung et al. |
| 2019/0343456 A1 | 11/2019 | Kahlert et al. |
| 2019/0369650 A1 | 12/2019 | Swanson et al. |
| 2019/0387972 A1 | 12/2019 | Hu et al. |
| 2019/0391243 A1 | 12/2019 | Nicolaescu |
| 2019/0391702 A1 | 12/2019 | Jo et al. |
| 2020/0003619 A1 | 1/2020 | Hu et al. |
| 2020/0011995 A1 | 1/2020 | Send et al. |
| 2020/0069225 A1 | 3/2020 | Vizbaras et al. |
| 2020/0100705 A1 | 4/2020 | Dellimore et al. |
| 2020/0143534 A1 | 5/2020 | Wright et al. |
| 2020/0158548 A1 | 5/2020 | Rice et al. |
| 2020/0196874 A1 | 6/2020 | Rozental et al. |
| 2020/0214602 A1 | 7/2020 | Narumi et al. |
| 2020/0237272 A1 | 7/2020 | Lin et al. |
| 2020/0249492 A1 | 8/2020 | Maes |
| 2020/0323440 A1 | 10/2020 | Vule et al. |
| 2020/0359948 A1 | 11/2020 | Dunn et al. |
| 2020/0397351 A1 | 12/2020 | Miyata |
| 2021/0000385 A1 | 1/2021 | Warren et al. |
| 2021/0022623 A1 | 1/2021 | Rice et al. |
| 2021/0028602 A1 | 1/2021 | Cao et al. |
| 2021/0161408 A1 | 6/2021 | Wakita |
| 2021/0186431 A1 | 6/2021 | Jung et al. |
| 2021/0267471 A1 | 9/2021 | Bonomi et al. |
| 2021/0321887 A1 | 10/2021 | Fukazawa et al. |
| 2021/0330202 A1 | 10/2021 | Konecky |
| 2021/0338083 A1 | 11/2021 | Sie et al. |
| 2021/0386310 A1 | 12/2021 | Hong et al. |
| 2021/0405518 A1 | 12/2021 | Lablans |
| 2022/0015649 A1 | 1/2022 | Ikuta et al. |
| 2022/0018762 A1 | 1/2022 | Ekin et al. |
| 2022/0019861 A1 | 1/2022 | Durr et al. |
| 2022/0039679 A1 | 2/2022 | Califa et al. |
| 2022/0061644 A1 | 3/2022 | Fontaine et al. |
| 2022/0104822 A1 | 4/2022 | Shelton, IV et al. |
| 2022/0117557 A1 | 4/2022 | Hsu et al. |
| 2022/0196557 A1 | 6/2022 | Zheng et al. |
| 2022/0211286 A1 | 7/2022 | Tank et al. |
| 2022/0265158 A1 | 8/2022 | Tokura |
| 2022/0370010 A1 | 11/2022 | Zilkie et al. |
| 2022/0413143 A1 | 12/2022 | Parsa et al. |
| 2023/0003938 A1 | 1/2023 | Zilkie et al. |
| 2023/0039055 A1 | 2/2023 | Gardner et al. |
| 2023/0048766 A1 | 2/2023 | Frey |
| 2023/0064006 A1 | 3/2023 | Kim et al. |
| 2023/0148885 A1 | 5/2023 | Bechtel et al. |
| 2023/0148886 A1 | 5/2023 | Bechtel et al. |
| 2023/0164444 A1 | 5/2023 | Yang |
| 2023/0225643 A1 | 7/2023 | Scofield et al. |
| 2023/0277062 A1 | 9/2023 | Dalvi et al. |
| 2023/0277075 A1 | 9/2023 | Pantelopoulos et al. |
| 2023/0296510 A1 | 9/2023 | Xu |
| 2023/0320598 A1 | 10/2023 | Khine et al. |
| 2023/0347029 A1 | 11/2023 | Corso et al. |
| 2023/0375525 A1 | 11/2023 | Merritt et al. |
| 2023/0397818 A1 | 12/2023 | Newhouse et al. |
| 2023/0401747 A1 | 12/2023 | Dunn et al. |
| 2024/0032790 A1 | 2/2024 | Patel et al. |
| 2024/0041342 A1 | 2/2024 | Lai et al. |
| 2024/0074667 A1 | 3/2024 | Rick et al. |
| 2024/0108289 A1 | 4/2024 | Bechtel et al. |
| 2024/0115212 A1 | 4/2024 | Jang |
| 2024/0156355 A1 | 5/2024 | O'Brien et al. |
| 2024/0298907 A1 | 9/2024 | Bechtel et al. |
| 2024/0350019 A1 | 10/2024 | Pery-Shechter et al. |
| 2024/0364420 A1 | 10/2024 | Vallius et al. |
| 2025/0169696 A1 | 5/2025 | Dunn et al. |

FOREIGN PATENT DOCUMENTS

| | | | |
|---|---|---|---|
| CN | 110301896 | B | 10/2019 |
| CN | 211094079 | U | 7/2020 |
| CN | 211131004 | U | 7/2020 |
| CN | 112639582 | A | 4/2021 |
| CN | 114466549 | A | 5/2022 |
| EP | 3 002 568 | A1 | 4/2016 |
| EP | 2 395 958 | B1 | 12/2017 |
| EP | 3 384 841 | A1 | 10/2018 |
| EP | 3 558119 | B1 | 11/2020 |
| EP | 3 886 686 | A0 | 10/2021 |
| EP | 3 903 676 | A1 | 11/2021 |

(56)                    References Cited

FOREIGN PATENT DOCUMENTS

| WO | WO 2018/029123 A1 | 2/2018 |
| WO | WO 2019/149815 A1 | 8/2019 |
| WO | WO 2019/233903 A1 | 12/2019 |
| WO | WO 2020/030641 A1 | 2/2020 |
| WO | WO 2020/114989 A1 | 6/2020 |
| WO | WO 2021/058338 A1 | 4/2021 |
| WO | WO 2021/094473 A1 | 5/2021 |
| WO | WO 2021/116766 A1 | 6/2021 |
| WO | WO 2021/116766 A8 | 6/2021 |
| WO | WO 2023/031927 A1 | 3/2023 |
| WO | WO 2023/245149 A2 | 12/2023 |
| WO | WO 2024/052289 A1 | 3/2024 |
| WO | WO 2024/173585 A1 | 8/2024 |

OTHER PUBLICATIONS

International Search Report and Written Opinion of the International Searching Authority, Mailed Dec. 11, 2024, Corresponding to PCT/IB2024/000388, 14 pages.

Abookasis, D. et al., "Feasibility study of hidden flow imaging based on laser speckle technique using multiperspectives contrast images", Optics and Lasers in Engineering, 2014, pp. 38-45.

Akram, M. N. et al., "Laser speckle reduction due to spatial and angular diversity introduced by fast scanning micromirror", Applied Optics, Jun. 4, 2010, pp. 3297-3304, vol. 49, No. 17, Optical Society of America.

Apsel, S. et al., "Rolling-Shutter Laser Speckle Analysis in Bio-Photonics", Proc. of SPIE, Jun. 20, 2024, pp. 130060U-1-130060U-4, vol. 13006, SPIE.

Baek, H. J. et al., "The Effect of Optical Crosstalk on Accuracy of Reflectance-Type Pulse Oximeter for Mobile Healthcare", Journal of Healthcare Engineering, Oct. 21, 2018, 9 pages, vol. 2018, Article ID 3521738, Hindawi, https://doi.org/10.1155/2018/3521738.

Baets, R. et al., "Spectroscopy-on-chip applications of silicon photonics", Proc. Of SPIE, 2013, pp. 862701-1 through 862701-10, vol. 8627, SPIE.

Berger, A. J. et al., "Feasibility of measuring blood glucose concentration by near-infrared Raman spectroscopy", Spectrochimica Acta Part A, 1997, pp. 287-292, Elsevier Science B.V.

Bi, R. et al., "A speckle-based method for fast blood flow measurement in deep tissue", Proceedings of SPIE, Optical Biopsy XIX: Toward Real-Time Spectroscopic Imaging and Diagnosis, Mar. 5, 2021, pp. 1163606-1 through 1163606-5, vol. 11636, SPIE.

Bi, R. et al., "Fast pulsatile blood flow measurement in deep tissue through a multimode detection fiber", Journal of Biomedical Optics, May 13, 2020, pp. 055003-1 through 055003-10, vol. 25(5), SPIE.

Biswas, A. et al., "Fast diffuse correlation spectroscopy with a low-cost, fiber-less embedded diode laser", Biomedical Optics Express, Oct. 4, 2021, pp. 6686-6700, vol. 12, No. 11, Optical Society of America.

Brouckaert, J., et al., "Silicon-on-Insulator Microspectrometer", Proceedings Symposium IEEE/LEOS Benelux Chapter, 2008, pp. 7-10, IEEE.

Cole, D. B. et al., "Integrated heterodyne interferometer with on-chip modulators and detectors", Optics Letters, Jun. 25, 2015, pp. 3097-3100, vol. 40, No. 13, Optical Society of America.

Epping, J. P. et al., "High power, tunable, narrow linewidth dual gain hybrid laser", Laser Congress, Oct. 3, 2019, pp. 1-2.

European Patent Office Communication pursuant to Article 94(3) EPC, for Patent Application No. 22776935.3, dated Jun. 24, 2025, 7 pages.

European Patent Office Communication pursuant to Rule 114(2) EPC, for Patent Application No. 22776935.3, mailed Aug. 9, 2024, 6 pages.

Fu, D. et al., "In Vivo Metabolic Fingerprinting of Neutral Lipids with Hyperspectral Stimulated Raman Scattering Microscopy", Journal of the American Chemical Society, May 28, 2014, pp. 8820-8828, American Chemical Society Publications.

Fukui, T. et al., "Single-Pixel Imaging Using Multimode Fiber and Silicon Photonic Phased Array", Journal of Lightwave Technology, Jul. 14, 2020, pp. 839-844, vol. 39, No. 3, IEEE.

Ge, Z. et al., "Dynamic laser speckle analysis using the event sensor", Applied Optics, Dec. 23, 2020, pp. 172-178, vol. 60, No. 1, Optical Society of America.

Goodman, J. W., "Some fundamental properties of speckle", Journal of the Optical Society of America, Nov. 1976, pp. 1145-1150, vol. 66, No. 11, Optical Society of America.

Gottschling, K. et al., "Molecular Insights into Carbon Dioxide Sorption in Hydrazone-Based Covalent Organic Frameworks with Tertiary Amine Moieties", Chemistry of Materials, Feb. 13, 2019, pp. 1946-1955, American Chemical Society.

Hashimoto, Y. et al., "Fabrication of an Anti-Reflective and Super-Hydrophobic Structure by Vacuum Ultraviolet Light-Assisted Bonding and Nanoscale Pattern Transfer", Micromachines, Apr. 15, 2018, pp. 1-11, www.mdpi.com/journal/micromachines.

Hollis, V. S. et al., "Non-invasive monitoring of brain tissue temperature by near-infrared spectroscopy", Proceedings of SPIE, Optical Tomography and Spectroscopy of Tissue IV, Jun. 29, 2001, pp. 470-481, vol. 4250, SPIE, |https://www.spiedigitallibrary.org/conference-proceedings-of-spie/4250/1/Noninvasivemonitoring-of-brain-tissue-temperature-by-near-infraredspectroscopy/10.1117/12.434506.short?SSO=1.

International Search Report and Written Opinion of the International Searching Authority, mailed Apr. 4, 2023, corresponding to PCT/EP2022/082341, 33 pages.

International Search Report and Written Opinion of the International Searching Authority, mailed Feb. 1, 2022, corresponding to PCT/IB2021/000649, 18 pages.

International Search Report and Written Opinion of the International Searching Authority, Mailed Mar. 11, 2021, Corresponding to PCT/IB2020/001037, 13 pages.

International Search Report and Written Opinion of the International Searching Authority, mailed Nov. 15, 2021, corresponding to PCT/IB2021/000517, 15 pages.

International Search Report and Written Opinion of the International Searching Authority, mailed Oct. 10, 2022, corresponding to PCT/IB2022/000373, 16 pages.

International Search Report and Written Opinion of the International Searching Authority, mailed Oct. 19, 2022, corresponding to PCT/EP2022/071467, 16 pages.

International Search Report and Written Opinion of the International Searching Authority, mailed Feb. 14, 2023, corresponding to PCT/EP2022/082162, 33 pages.

International Search Report and Written Opinion of the International Searching Authority, mailed Jan. 2, 2023, corresponding to PCT/EP2022/074876, 13 pages.

International Search Report and Written Opinion of the International Searching Authority, mailed Jun. 23, 2025, corresponding to PCT/IB2025/000070, 15 pages.

International Search Report and Written Opinion of the International Searching Authority, mailed May 14, 2025, corresponding to PCT/IB2025/000071, 15 pages.

Invitation to Pay Additional Fees and Partial Search Report mailed Feb. 14, 2023 in related International Application No. PCT/EP2022/082341, 18 pages.

Izutsu, M. et al., "Integrated Optical SSB Modulator/Frequency Shifter", IEEE Journal of Quantum Electronics, Nov. 1981, pp. 2225-2227, vol. QE-17, No. 11, IEEE.

Kang, J. W. et al., "Direct observation of glucose fingerprint using in vivo Raman spectroscopy," Science Advances, Jan. 24, 2020, pp. 1-8, American Association for the Advancement of Science.

Karlsson, C. J. et al., "All-fiber multifunction continuous-wave coherent laser radar at 1.55 $\mu$m for range, speed, vibration, and wind measurements", Applied Optics, Jul. 20, 2000, pp. 3716-3726, vol. 39, No. 21, Optical Society of America.

Lai, M. et al., "Perfusion Monitoring By Contactless Photoplethysmography Imaging", 2019 IEEE 16th International Symposium on Biomedical Imaging (ISBI 2019), Venice, Italy, Apr. 8-11, 2019, pp. 1778-1782, IEEE.

(56) References Cited

OTHER PUBLICATIONS

Lai, N. et al., "CO2 Capture With Absorbents of Tertiary Amine Functionalized Nano-SiO2", Frontiers in Chemistry, Feb. 28, 2020, pp. 1-9, vol. 8, Article 146, www.frontiersin.org.

Lapchuk, A. et al., "Investigation of speckle suppression beyond human eye sensitivity by using a passive multimode fiber and a multimode fiber bundle", Applied Optics, Feb. 21, 2020, pp. 6820-6834, vol. 28, No. 5, Optical Society of America.

Liu, X. et al., "Simultaneous measurements of tissue blood flow and oxygenation using a wearable fiber-free optical sensor", Journal of Biomedical Optics, Jan. 29, 2021, pp. 012705-1 through 012705-15, vol. 26, No. 1, SPIE.

Loi, R. et al., "Transfer Printing of AlGaInAs/InP Etched Facet Lasers to Si Substrates", IEEE Photonics Journal, Nov. 11, 2016, 11 pages, vol. 8, No. 6, IEEE.

Lu, H. et al., "Single-trial estimation of the cerebral metabolic rate of oxygen with imaging photoplethysmography and laser speckle contrast imaging", Optics Letters, Mar. 17, 2015, pp. 1193-1196, vol. 40, No. 7, Optical Society of America.

Mehta, D. S. et al., "Laser speckle reduction by multimode optical fiber bundle with combined temporal, spatial, and angular diversity", Applied Optics, Apr. 11, 2012, pp. 1894-1904, vol. 51, No. 12, Optical Society of America.

Merritt, S. et al., "Monitoring temperature non-invasively using broadband Diffuse Optical Spectroscopy", OSA/FIO, 2004, 1 page, Optical Society of America, https://opg.optica.org/abstract.cfm?URI=FiO-2004-FTuK4.

Mosso, E. et al., "Cluster speckle structures through multiple apertures forming a closed curve", Optics Communications, 2010, pp. 1285-1290, Elsevier B.V.

Nabeel, P. M. et al., "Local Pulse Wave Velocity: Theory, Methods, Advancements, and Clinical Applications", IEEE Reviews in Biomedical Engineering, Jul. 29, 2019, pp. 74-112, vol. 13, IEEE.

Noriki, A. et al., "45-degree curved micro-mirror for vertical optical I/O of silicon photonics chip", Optics Express, Jul. 1, 2019, pp. 19749-19757, vol. 27, No. 14, Optical Society of America, https://doi.org/10.1364/OE.27.019749.

Poulton, C. V. et al., "Frequency-modulated Continuous-wave LIDAR Module in Silicon Photonics", OFC, 2015, 4 pages, Optical Society of America.

Qiu, J. et al., "Correcting speckle contrast at small speckle size to enhance signal to noise ratio for laser speckle contrast imaging", Optics Express, Nov. 15, 2013, pp. 28902-28913, vol. 21, No. 23, Optical Society of America.

Redding, B. et al., "Compact spectrometer based on a disordered photonic chip", Nature Photonics, Jul. 28, 2013, pp. 746-751, vol. 7, Macmillan Publishers Limited.

Redding, B. et al., "Evanescently coupled multimode spiral spectrometer", Optica, Aug. 25, 2016, pp. 956-962, vol. 3, No. 9, Optical Society of America.

Robinson, M. B., "Interferometric diffuse correlation spectroscopy improves measurements at long source-detector separation and low photon count rate", Journal of Biomedical Optics, Sep. 30, 2020, pp. 097004-1 through 097004-12, vol. 25, No. 9, SPIE.

Roelkens, G. et al., "Transfer printing for silicon photonics transceivers and interposers", 2018 IEEE Optical Interconnects Conference, Jun. 4, 2018, pp. 13-14, IEEE.

Ryckeboer, E., "Spectroscopic Detection of Glucose with a Silicon Photonic Integrated Circuit", Universiteit Gent, Jan. 1, 2014, 263 pages, ISBN 978-90-8578-688-7, http://www.photonics.intec.ugent.be/download/phd_206.pdf.

Schneider, S. et al., "Optical coherence tomography system mass-producible on a silicon photonic chip", Optics Express, Jan. 20, 2016, pp. 1573-1586, vol. 24, No. 2, Optical Society of America.

Sdobnov, A. Y. et al. "Speckle dynamics under ergodicity breaking",Â Journal of Physics D: Applied Physics, Mar. 26, 2018, pp. 1-21, vol. 51, No. 15, IOP Publishing Ltd.

Shimotsu, S. et al., "Single Side-Band Modulation Performance of a LiNbO3 Integrated Modulator Consisting of Four-Phase Modulator Waveguides", IEEE Photonics Technology Letters, Apr. 2001, pp. 364-366, vol. 13, No. 4, IEEE.

Subramanian, A. Z. et al., "Silicon and silicon nitride photonic circuits for spectroscopic sensing on-a-chip [Invited]", Photon. Res., Aug. 28, 2015, pp. B47-B59, vol. 3, No. 5, Chinese Laser Press.

Teng, Z. et al., "In Vivo Pulse Wave Measurement Through a Multimode Fiber Diffuse Speckle Analysis System", Frontiers in Physics, Jan. 19, 2021, pp. 1-8, vol. 8, Article 613342, www.frontiersin.org.

Timm, U. et al., "Non-Invasive Optical Real-time Measurement of Total Hemoglobin Content", Procedia Engineering, 2010, pp. 488-491, Elsevier Ltd.

Tran, T-T-K. et al., "Speckle reduction in laser projection displays through angle and wavelength diversity", Applied Optics, Feb. 16, 2016, pp. 1267-1274, vol. 55, No. 6, Optical Society of America.

Tuchin, V., "Chapter 8: Coherent Effects at the Interaction of Laser Radiation with Tissues and Cell Flows", Tissue Optics Light Scattering Methods and Instruments for Medical Diagnostics, 3rd Edition, 2015, pp. 359-417, SPIE.

U.S. Advisory Action for U.S. Appl. No. 17/822,419, dated May 2, 2024, 5 pages.

U.S. Advisory Action for U.S. Appl. No. 17/822,419, dated Oct. 10, 2023, 6 pages.

U.S. Appl. No. 18/984,845, filed Dec. 17, 2024.

U.S. Appl. No. 18/991,054, filed Dec. 20, 2024.

U.S. Appl. No. 19/275,916, filed Jul. 21, 2025.

U.S. Notice of Allowance for U.S. Appl. No. 17/703,920, dated Jul. 31, 2024, 10 pages.

U.S. Notice of Allowance from U.S. Appl. No. 17/757,130, dated Jan. 18, 2023, 10 pages.

U.S. Notice of Allowance from U.S. Appl. No. 17/822,419, dated Nov. 6, 2024, 10 pages.

U.S. Office Action for U.S. Appl. No. 17/703,920, dated Apr. 5, 2024, 11 pages.

U.S. Office Action for U.S. Appl. No. 17/822,419, dated Feb. 20, 2024, 12 pages.

U.S. Office Action for U.S. Appl. No. 17/822,419, dated Jun. 12, 2024, 12 pages.

U.S. Office Action for U.S. Appl. No. 17/822,419, dated Nov. 3, 2023, 18 pages.

U.S. Office Action from U.S. Appl. No. 17/711,974, dated Oct. 11, 2024, 18 pages.

U.S. Office Action from U.S. Appl. No. 17/822,419, dated Jul. 20, 2023, 21 pages.

U.S. Office Action from U.S. Appl. No. 17/822,419, dated Mar. 10, 2023, 17 pages.

U.S. Office Action from U.S. Appl. No. 17/934,502, dated Aug. 31, 2023, 6 pages.

U.S. Office Action from U.S. Appl. No. 17/934,502, dated Feb. 1, 2024, 6 pages.

U.S. Office Action from U.S. Appl. No. 17/934,502, dated Jun. 5, 2024, 7 pages.

U.S. Office Action from U.S. Appl. No. 18/984,845, dated Mar. 3, 2025, 7 pages.

U.S. Office Action from U.S. Appl. No. 18/991,054, dated Jun. 24, 2025, 23 pages.

U.S. Office Action from U.S. Appl. No. 18/991,054, dated Mar. 3, 2025, 19 pages.

Valley, G.C. et al., "Multimode waveguide speckle patterns for compressive sensing", Optics Letters, May 23, 2016, pp. 2529-2532, vol. 41, No. 11, Optical Society of America.

Van Gastel, M. et al., "Camera-based pulse-oximetry—validated risks and opportunities from theoretical analysis", Biomedical Optics Express, Dec. 5, 2017, pp. 102-119, vol. 9, No. 1, Optical Society of America.

Website: "0.07mm Dia., TO-46 Package, InGaAs Photodiode", 2022, printed Dec. 7, 2022, 1 page, Edmund Optics Inc., https://www.edmundoptics.com/p/ingaas-detector-70mum-dia-to-46/12571/.

Website: "FlowMet Peripheral Blood Flow Monitoring System", updated Oct. 2022, printed Dec. 7, 2022, 7 pages, https://www.

(56)　　　　　References Cited

OTHER PUBLICATIONS medtronic.com/us-en/healthcare-professionals/products/cardiovascular/intraprocedural-monitoring/flowmet.html.

Website: "Optical Solutions", Molex, dated 2023, printed May 10, 2023, 13 pages, Molex, LLC, https://www.molex.com/en-us/products/optical-solutions.

Website: "Track Your SpO2 to Uncover Changes in Your Wellbeing", Fitbit News, dated Sep. 7, 2020, printed Apr. 17, 2023, 7 pages, Fitbit, Inc., https://blog.fitbit.com/track-your-spo2/).626.

Wenz, J. J., "Examining water in model membranes by near infrared spectroscopy and multivariate analysis", BBA—Biomembranes, Dec. 9, 2017, pp. 673-682, Elsevier B.V., https://www.sciencedirect.com/science/article/pii/S0005273617303905.

Xu, J. et al., "Interferometric speckle visibility spectroscopy (ISVS) for human cerebral blood flow monitoring", APL Photonics, Dec. 4, 2020, pp. 126102-1 through 126102-10, vol. 5. AIP Publishing.

Xu, M. et al., "Laser Speckle Reduction Using a Motionless Despeckle Element Based on Random Mie Scattering", Journal of Display Technology, Nov. 12, 2013, pp. 151-156, vol. 10, No. 2, IEEE.

Yamakoshi, Y. et al., "Side-scattered finger-photoplethysmography: experimental investigations toward practical noninvasive measurement of blood glucose", Journal of Biomedical Optics, Jun. 2017, pp. 067001-1 through 067001-11, vol. 22, No. 6, SPIE.

Yao, Z. et al., "Integrated Silicon Photonic Microresonators: Emerging Technologies", IEEE Journal of Selected Topics in Quantum Electronics, Jun. 11, 2018, 24 pages, vol. 24, No. 6, IEEE.

Zalevsky, Z. et al., "Novel Approaches for Near and Far Field Super Resolved Imaging", 22nd Congress of the International Commision for Optics: Light for the Development of the World, Proc. of SPIE, Sep. 15, 2011, pp. 80116M-1 through 80116M-11, vol. 8011, No. 1, SPIE.

Zhang, J. et al., "III-V-on-Si photonic integrated circuits realized using micro-transfer-printing", APL Photonics, Nov. 4, 2019, pp. 110803-1 through 110803-10.

Zijlstra, W. G. et al., "Absorption Spectra of Human Fetal and Adult Oxyhemoglobin, De-Oxyhemoglobin, Carboxyhemoglobin, and Methemoglobin", Clinical Chemistry, Sep. 1991, pp. 1633-1638, vol. 37, No. 9, https://academic.oup.com/clinchem/article-abstract/37/9/1633/5649610?redirectedFrom=fulltext.

Zilkie, A. J. et al., "Multi-Micron Silicon Photonics Platform for Highly Manufacturable and Versitile Photonic Integrated Circuits", IEEE Journal of Selected Topics in Quantum Electronics, Apr. 15, 2019, 13 pages, vol. 25, No. 5, IEEE.

Zilkie, A. J. et al., "Power-efficient III-V/Silicon external cavity DBR lasers", Optics Express, Sep. 27, 2012, pp. 23456-23462, vol. 20, No. 21, Optical Society of America.

"NanEye Miniature Camera Module", ams Datasheet, Feb. 23, 2021, pp. 1-34, www.mouser.com.

Chen, Hsiang-Lin et al., "A CMOS Imager for Reflective Pulse Oximeter with Motion Artifact and Ambient Interference Rejections", 2018 IEEE Asian Solid-State Circuits Conference, Nov. 5-7, 2018, Taiwan, pp. 25-26, IEEE.

International Search Report and Written Opinion of the International Searching Authority, mailed Oct. 7, 2025, corresponding to PCT/IB2025/000235, 18 pages.

Invitation to Pay Additional Fees and Partial International Search of the International Searching Authority, mailed Aug. 14, 2025, corresponding to PCT/IB2025/000235, 16 pages.

U.S. Appl. No. 19/390,480, filed Nov. 14, 2025.

U.S. Appl. No. 19/426,008, filed Dec. 18, 2025.

* cited by examiner

SYSTEM AND METHOD FOR MEASURING BLOOD PRESSURE

CROSS-REFERENCE TO RELATED APPLICATION(S)

The present application claims priority to and the benefit of U.S. Provisional Application No. 63/514,994, filed Jul. 21, 2023, entitled "CUFF-BASED BLOOD PRESSURE MEASUREMENT USING BLOOD FLOW", the entire content of which is incorporated herein by reference.

FIELD

One or more aspects of embodiments according to the present disclosure relate to health monitoring, and more particularly to a system and method for measuring blood pressure.

BACKGROUND

Blood pressure may be a useful biomarker for a subject, for example as a general indicator of some aspects of the health of the subject, or as a diagnostic tool when investigating illness.

It is with respect to this general technical environment that aspects of the present disclosure are related.

SUMMARY

According to an embodiment of the present disclosure, there is provided a system, including: a speckleplethysmography sensor; and a processing circuit, the system being configured: to perform, using the speckleplethysmography sensor, blood flow measurements of a subject, and measurements of cuff pressure of a cuff worn by the subject, while the cuff pressure varies; and to calculate, from the blood flow measurements and the cuff pressure measurements, a first blood pressure.

In some embodiments: the first blood pressure is a systolic pressure, and the calculating of the first blood pressure includes calculating the first blood pressure using speckleplethysmography pulse detection.

In some embodiments: the first blood pressure is a systolic pressure, and the calculating of the first blood pressure includes calculating the first blood pressure using a low-frequency speckleplethysmography method.

In some embodiments: the first blood pressure is a systolic pressure, and the calculating of the first blood pressure includes: calculating a first value of the first blood pressure using speckleplethysmography pulse detection; and calculating a second value of the first blood pressure using a low-frequency speckleplethysmography method.

In some embodiments, the calculating of the first blood pressure further includes calculating a weighted sum of the first value of the first blood pressure and of the second value of the first blood pressure.

In some embodiments: the first blood pressure is a systolic pressure, and the system is further configured to calculate, from the blood flow measurements and the cuff pressure measurements, a diastolic blood pressure.

In some embodiments, the calculating of the diastolic blood pressure includes calculating the diastolic blood pressure using pulse template matching.

In some embodiments, the calculating of the diastolic blood pressure includes calculating the diastolic blood pressure using maximum amplitude detection.

In some embodiments, the calculating of the diastolic blood pressure includes: calculating a first value of the diastolic blood pressure using pulse template matching; and calculating a second value of the diastolic blood pressure using maximum amplitude detection.

In some embodiments, the calculating of the diastolic blood pressure further includes calculating a weighted sum of the first value of the diastolic blood pressure and of the second value of the diastolic blood pressure.

According to an embodiment of the present disclosure, there is provided a method, including: measuring a first blood pressure, the measuring of the first blood pressure including: varying a cuff pressure of a cuff on an appendage of a subject; generating a speckleplethysmography signal from a speckleplethysmography sensor on the appendage; and determining the first blood pressure based on the speckleplethysmography signal and based on the cuff pressure.

In some embodiments: the first blood pressure is a systolic blood pressure, and the determining of the first blood pressure includes: decreasing the cuff pressure; and determining the cuff pressure at a point in time at which a measure of blood flow, based on the speckleplethysmography signal, indicates an increase in blood flow.

In some embodiments, the measure of blood flow is based on a method of pulse detection.

In some embodiments, the method of pulse detection includes: calculating a measure of quality of a candidate pulse; and assessing whether the candidate pulse is part of a sequence of pulses.

In some embodiments, the assessing of whether the candidate pulse is part of a sequence of pulses includes: determining whether an amplitude of the candidate pulse is consistent with an amplitude trend within the sequence of pulses, and determining whether a position in time of the candidate pulse is consistent with positions in time of the sequence of pulses.

In some embodiments, the measure of blood flow is based on a low-frequency speckleplethysmography method.

In some embodiments, the measure of blood flow is further based on a method of pulse detection.

In some embodiments: the first blood pressure is a diastolic blood pressure, and the determining of the first blood pressure includes: decreasing the cuff pressure; and determining the cuff pressure at a point in time at which the speckleplethysmography signal has a maximum amplitude.

In some embodiments: the first blood pressure is a diastolic blood pressure, and the determining of the first blood pressure includes: decreasing the cuff pressure; and determining the cuff pressure at a point in time at which a discrepancy between the speckleplethysmography signal and a template waveform is less than a threshold.

In some embodiments: the first blood pressure is a diastolic blood pressure, and the determining of the first blood pressure includes: decreasing the cuff pressure; and determining the cuff pressure at a point in time at which a low-frequency speckleplethysmography signal ceases to increase.

BRIEF DESCRIPTION OF THE DRAWINGS

These and other features and advantages of the present disclosure will be appreciated and understood with reference to the specification, claims, and appended drawings wherein:

DETAILED DESCRIPTION

Figure 1:
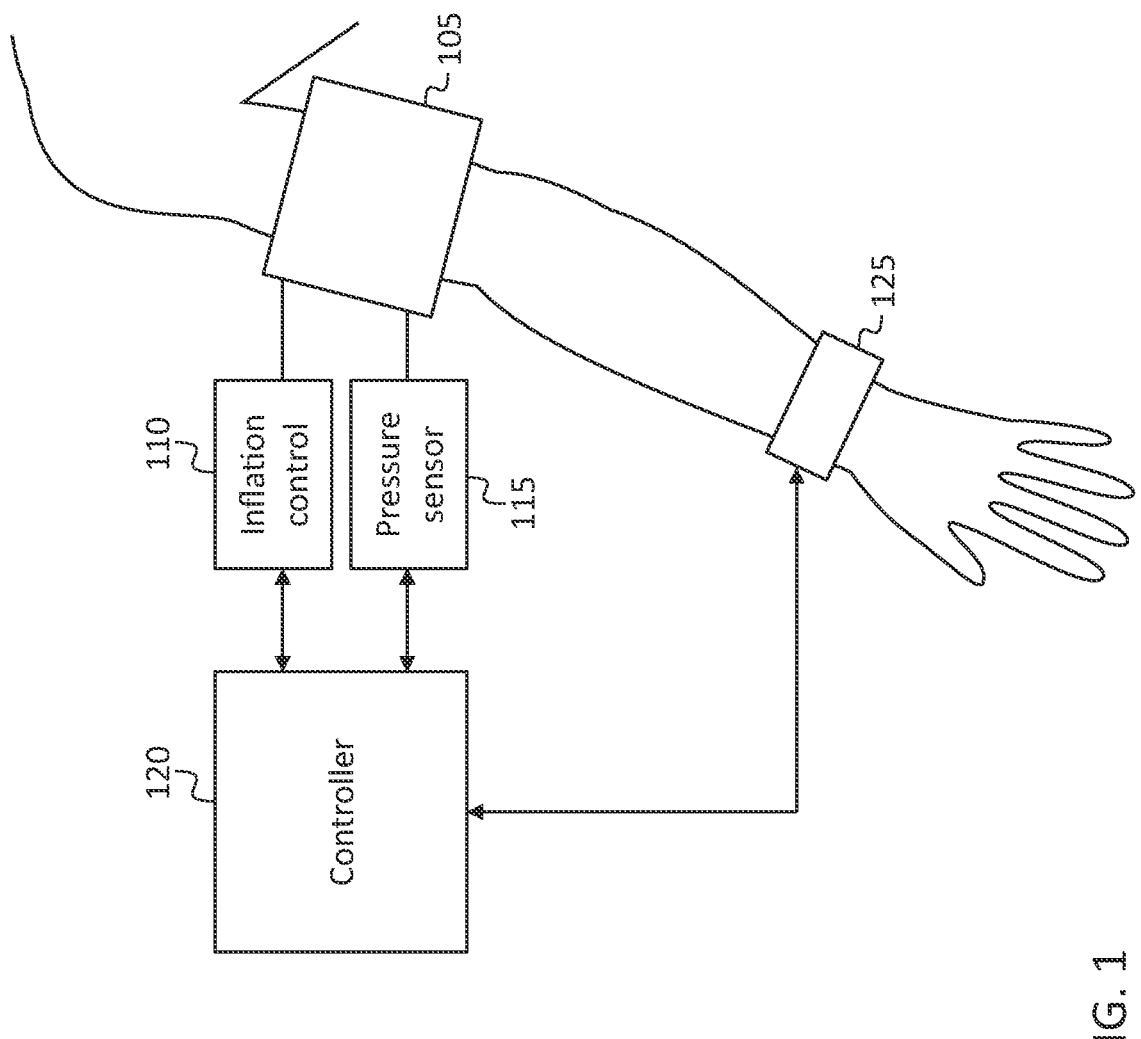
FIG. 1 is a schematic drawing of an arm of a subject and a system for measuring blood pressure, according to an embodiment of the present disclosure.

The detailed description set forth below in connection with the appended drawings is intended as a description of exemplary embodiments of a system and method for measuring blood pressure provided in accordance with the present disclosure and is not intended to represent the only forms in which the present disclosure may be constructed or utilized. The description sets forth the features of the present disclosure in connection with the illustrated embodiments. It is to be understood, however, that the same or equivalent functions and structures may be accomplished by different embodiments that are also intended to be encompassed within the scope of the disclosure. As denoted elsewhere herein, like element numbers are intended to indicate like elements or features.

Various methods may be employed to measure the blood pressure of a subject. For example, a blood pressure cuff (e.g., an inflatable cuff (containing an inflatable pneumatic bladder) that may be secured around the upper arm to apply pressure to the upper arm, the pressure corresponding to the (pneumatic) pressure in the cuff) may be attached to the upper arm of the subject, the cuff may be inflated until arterial blood flow ceases, and then the cuff may be gradually deflated, while monitoring the pressure in the cuff; the systolic (blood) pressure may then be read from the pressure sensor as the pressure during the first phase of the Korotkoff sound (K1), and the diastolic (blood) pressure may be read from the pressure sensor as the pressure during the fifth phase of the Korotkoff sound (K5).

In another method, a blood pressure cuff may be inflated or deflated, and while the pressure in the cuff is gradually increased or decreased, the cuff pressure (e.g., the pneumatic pressure in the cuff) may be measure with sufficient precision and bandwidth to detect pressure fluctuations in the cuff due to the fluctuations, with the cardiac cycle, of arterial pressure (e.g., the arterial pressure in the brachial artery). The amplitude of these cuff pressure fluctuations may be small or zero both when the cuff pressure is sufficiently high to prevent blood flow in the brachial artery and when the cuff pressure is sufficiently low that the pressure of the cuff on the arm is small and, as a result, arterial pressure fluctuations have little effect on the cuff pressure. At some point between these two cuff pressure extremes the fluctuations in cuff pressure may have maximum amplitude; the mean cuff pressure at which the amplitude is maximum, referred to herein as the "pressure at maximum amplitude" may be used as an approximate measurement of the mean arterial pressure, which is defined herein to be equal to ⅓ of the systolic pressure plus ⅔ of the diastolic pressure. In this context "mean cuff pressure" is an average of the (fluctuating) cuff pressure, e.g., the time average over one or more cardiac cycles, or the average of the maximum and minimum cuff pressure during a cardiac cycle.

In some embodiments, blood flow rate downstream from the cuff (in the direction of arterial blood flow) may be used in combination with adjustments to, and measurements of, the cuff pressure, to perform blood pressure measurements, as discussed in further detail below. Such blood pressure measurements may be used, for example, to improve the accuracy of blood pressure measurements made using the cuff alone (e.g., by obtaining a calibration of the cuff), or to improve the accuracy of blood pressure measurements made using another blood pressure measuring system (which may be calibrated using the system and methods disclosed herein). Such a blood pressure measuring system may be a system using (i) one or more plethysmography sensors or (ii) one or more plethysmography sensors and one or more speckleplethysmography sensors. The system and methods described herein may be capable of obtaining blood pressure measurements (e.g., measurements of systolic pressure and of diastolic pressure) with higher accuracy than, e.g., systems using only a cuff, and, as such, the system and methods described herein provide an improvement in the technology of blood pressure measurement.

FIG. 1 shows a system for measuring blood pressure, in some embodiments. A cuff 105 is secured around the upper arm of a subject. The cuff 105 is connected to an inflation control system 110, which may include a pump and one or more valves (e.g. metering valves) or flow meters for (i) pumping air into the cuff to increase the cuff pressure or (ii) decreasing the cuff pressure by allowing the cuff to deflate (by allowing air to escape, from the cuff, into the atmosphere). The rate of inflation or deflation may be controlled by, e.g., adjusting the speed of the pump, or opening or closing metering valves in the inflation control system 110. A pressure sensor 115 (which may have sufficient precision and bandwidth to detect pressure fluctuations in the cuff due to fluctuations, with the cardiac cycle, in arterial pressure) is connected by a pneumatic connection (e.g., integrated into) the pneumatic bladder of the cuff 105, and measures the pressure in the cuff 105 (e.g., in the pneumatic bladder of the cuff 105).

A controller 120 (which may be a processing circuit (discussed in further detail below)) is connected to the inflation control system 110 and to the pressure sensor 115. The processing circuit may control the inflation and deflation of the cuff 105, e.g., it may cause the pressure to increase or decrease smoothly (at a substantially constant rate) and monotonically (except for pressure fluctuations in the cuff due to the fluctuations, with the cardiac cycle, of arterial pressure) during inflation and deflation. In some embodiments the controller 120 includes a feedback controller (e.g., a feedback controller implemented in software or firmware) that receives a pressure signal from the pressure sensor 115 and that performs closed-loop control of the cuff pressure, to cause the cuff pressure to follow a pressure setpoint (e.g., a pressure setpoint that is increasing or decreasing at a constant rate).

A sensor for measuring blood flow velocity may be attached to the arm of the subject at a point downstream (for arterial flow) of the cuff 105. This sensor may be or include a speckleplethysmography sensor 125. The speckleplethysmography sensor 125 may include (i) a coherent light source (e.g., a semiconductor laser) for illuminating the tissue of the subject, including an artery that is downstream of the cuff

105, and (ii) an image sensor for receiving light that has interacted with (e.g., scattered from) the tissue, including the blood in the artery. The light that has interacted with the tissue and blood in the artery may form a speckle pattern on the image sensor. The speckle pattern may change as the blood moves in the artery; the rate at which the speckle pattern changes may depend on (e.g., be proportional to) the blood flow velocity. The measured image contrast, also called speckle contrast (e.g., the speckle contrast measured by the image sensor), may decrease as the blood flow velocity (and the rate of change of the speckle pattern) increases, because the changes in the speckle pattern due to moving scatterers occur faster than the integration time for each exposure. As such, the measured speckle contrast may depend on the blood flow velocity, and may be used to measure the blood flow velocity. The measured speckle contrast may also be affected by spatial integration over the area of each pixel of the image sensor (e.g., by the speckle-pixel size ratio), by temporal integration over the exposure time of each exposure, and by laser coherence and polarization. The measured blood flow velocity may be a discrete-time (sampled) signal with a sample rate equal to the frame rate of the image sensor (e.g., a sample rate of between 10 Hz and 1000 Hz).

Figure 2:
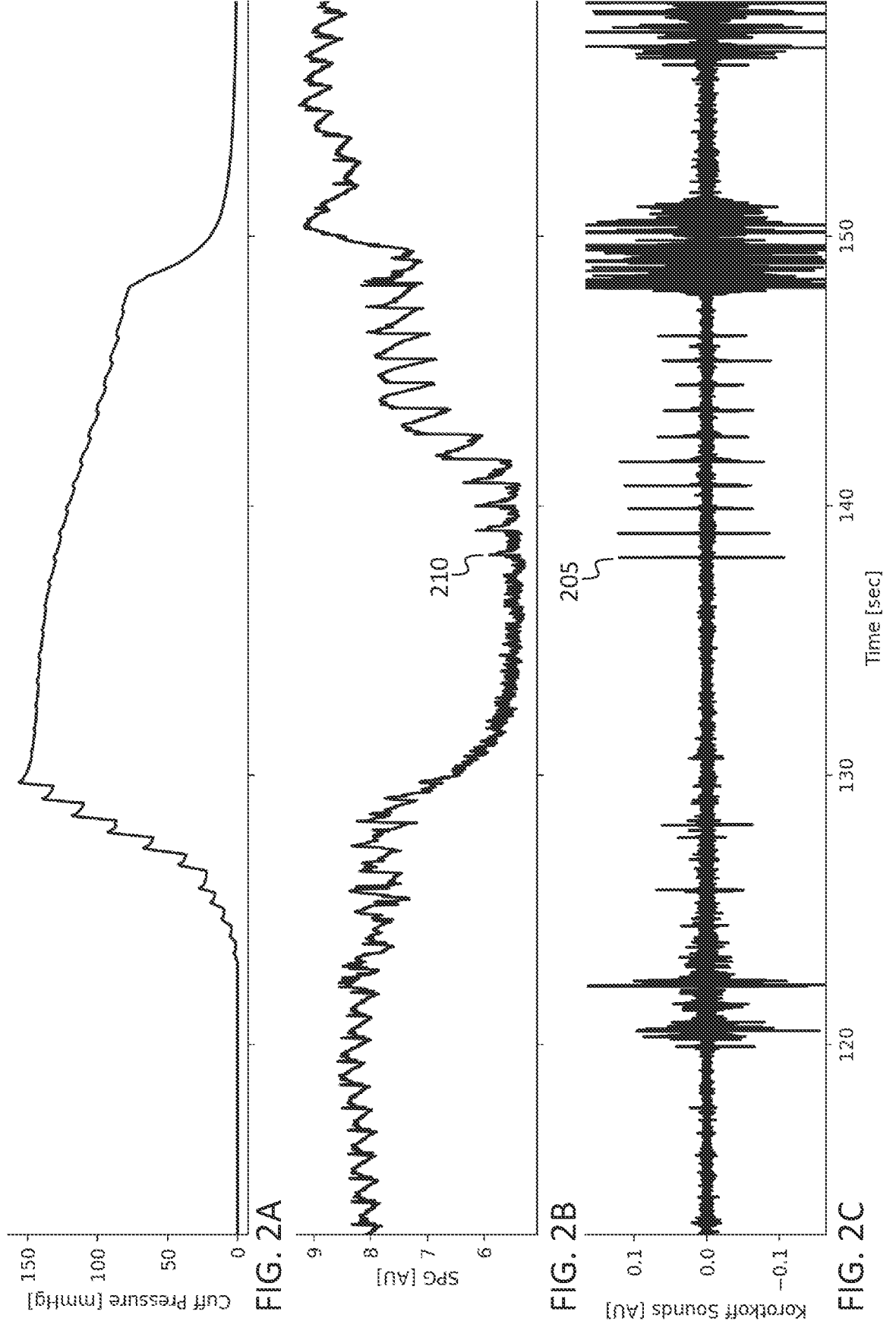
FIG. 2A is a graph of cuff pressure, according to an embodiment of the present disclosure.
FIG. 2B is a graph of blood flow velocity, according to an embodiment of the present disclosure.
FIG. 2C is a graph of Korotkoff sounds, according to an embodiment of the present disclosure.

FIGS. 2A-2C show the cuff pressure (FIG. 2A), the arterial blood flow velocity, measured by speckleplethysmography (SPG) (FIG. 2B), and the Korotkoff sounds (FIG. 2C), in one example of the inflation and deflation of the cuff 105. It may be seen from FIGS. 2A-2C that fluctuations, with the cardiac cycle, in the blood flow velocity cease when the cuff pressure is sufficiently high (e.g., sufficiently high to stop arterial blood flow) and that when cuff pressure is reduced, e.g. through deflation, the first Korotkoff sound 205 approximately coincides with a local peak 210, representing a heartbeat, in the blood flow velocity as measured by speckleplethysmography. The instantaneous blood flow velocity may vary with time, and may differ, at any time in the cardiac cycle, from the average blood flow velocity (which may also be referred to as the low-frequency blood flow velocity).

Systolic pressure may be measured, via the system of FIG. 1, using several methods. Such methods may include increasing the cuff pressure sufficiently high to stop arterial flow, then decreasing the cuff pressure, and determining the cuff pressure at a point in time at which a measure of blood flow, based on the speckleplethysmography signal, indicates a temporary local increase in blood flow representing at least a portion of the cardiac cycle. In a first method for measuring systolic pressure, speckleplethysmography pulse detection is used to detect an increase in blood flow by detecting the first pulse during cuff deflation, and the cuff pressure at that time (e.g., the mean cuff pressure at the time of the first detected pulse, or the instantaneous cuff pressure at the time of the first detected pulse) may be used as the measured systolic pressure.

As used herein, "pulse detection" means the detection of a blood flow velocity signal that is caused by a cardiac cycle (e.g., that is not caused by other mechanisms, e.g., by noise). As such, pulse detection may involve detecting (e.g., distinguishing from noise) the blood flow velocity peak corresponding to the ventricular systole, or it may involve detecting (e.g., distinguishing from noise) a waveform corresponding to an entire cardiac cycle. Similarly the "pulse" being detected may be a portion (e.g., a peak corresponding to the ventricular systole) of a cardiac cycle or an entire cardiac cycle.

Pulse detection may be performed using any of, or any combination of, several methods. In a first method, a time interval (e.g., an interval having a length approximately equal to the length of a cardiac cycle) may be selected as a candidate pulse. This selection may involve, for example, selecting a time interval that includes a local peak in the blood flow velocity signal. The candidate pulse may then be assessed using one or more methods, and a determination may be made, as to whether the candidate pulse is a pulse, based on the assessments. For example, one or more of various measures of the quality (or "quality metrics") of a candidate pulse may be applied to the candidate pulse. Examples of quality metrics include (i) whether the time between the candidate pulse and an adjacent detected pulse is less than a threshold interval (e.g., less than 1.75 seconds), (ii) whether the amplitude (e.g., the peak-to-peak amplitude) of the candidate pulse is at least a certain fraction (e.g., at least 15%) of the pre-inflation pulse amplitude, (iii) whether the rise time of the blood flow velocity peak (e.g., the 25%-75% rise time) is less than a certain fraction (e.g., less than 50%) of the inter-pulse interval, (iv) whether the number of zero crossings in the candidate pulse (e.g., in the blood flow velocity corresponding to the candidate pulse) is less than a threshold (e.g., whether there are fewer than 5 zero crossings) and (v) whether the Euclidian distance between the candidate pulse and an adjacent detected pulse is less than a threshold distance (e.g., less than 0.2 of the peak-to-peak amplitude of the candidate pulse or less than 0.2 of the peak-to-peak amplitude of the adjacent detected pulse). As used herein, the "Euclidean distance" is the square root of the sum of the squares of the sample-to-sample differences.

In a second method, pulse detection may include assessing whether the candidate pulse is part of a sequence of detected pulses. This may involve, for example, assessing whether the position in time of the candidate pulse is consistent with positions in time of the sequence of detected pulses. For example, a feature (e.g., the onset of the systolic peak, or the peak value of the systolic peak) in the blood flow velocity signal may be identified for the candidate pulse, and its position in time may be compared to the position in time it would be at if it were part of a regularly spaced sequence of pulses, the regularly spaced sequence of pulses being a hypothetical set of regular pulses fit (by adjusting the frequency and phase of the hypothetical set of pulses) to the sequence of detected pulses. The measure of quality of the candidate pulse, using this method, may be higher the closer the position in time is to the hypothetical position it would have in the hypothetical set of regular pulses. For example, if the offset between the position in time of the candidate pulse and the hypothetical position is less than a threshold (where the threshold may be, e.g., between 0.05 and 0.35 of the inter-pulse interval of the hypothetical set of regular pulses), then (and only then) the candidate pulse may be determined to be a pulse. In some embodiments, a candidate pulse is determined to be a pulse only if the position in time of the candidate pulse is near (e.g., if it precedes by one inter-pulse interval) the first detected pulse of the sequence of detected pulses. In some embodiments, combinations of the methods disclosed herein may be used to determine whether a candidate pulse is a pulse. For example, each of the methods disclosed herein may be used to generate a score for the candidate pulse (based on a respective measure of quality), and the candidate pulse may then be determined to be a pulse if and only if a weighted average of the scores exceeds a threshold.

As another example, the assessing of whether the candidate pulse is part of a sequence of pulses may include determining whether an amplitude of the candidate pulse is consistent with an amplitude trend within a sequence of detected pulses. For example, in some embodiments, pulses are first detected after the cuff pressure has fallen below the systolic pressure (e.g., because the amplitude of the pulses may increase after the cuff pressure falls below the systolic pressure, causing such later pulses to be more readily detectable). The system may then re-analyze the blood flow velocity signal obtained before the first detected pulse and attempt to detect one or more additional pulses, using the timing of the already-detected pulses to aid in the detection of such earlier pulses. The earlier pulses may then be detected, e.g., based on their positions in time (as discussed above) or also (or instead) based on their amplitudes. For example, because the amplitude of the pulses is expected to increase initially, after the cuff pressure falls below the systolic pressure, a candidate pulse that has a larger (peak to peak) amplitude than the next detected pulse may be determined not to be a pulse (and, e.g., to have been caused by noise).

Figure 3:
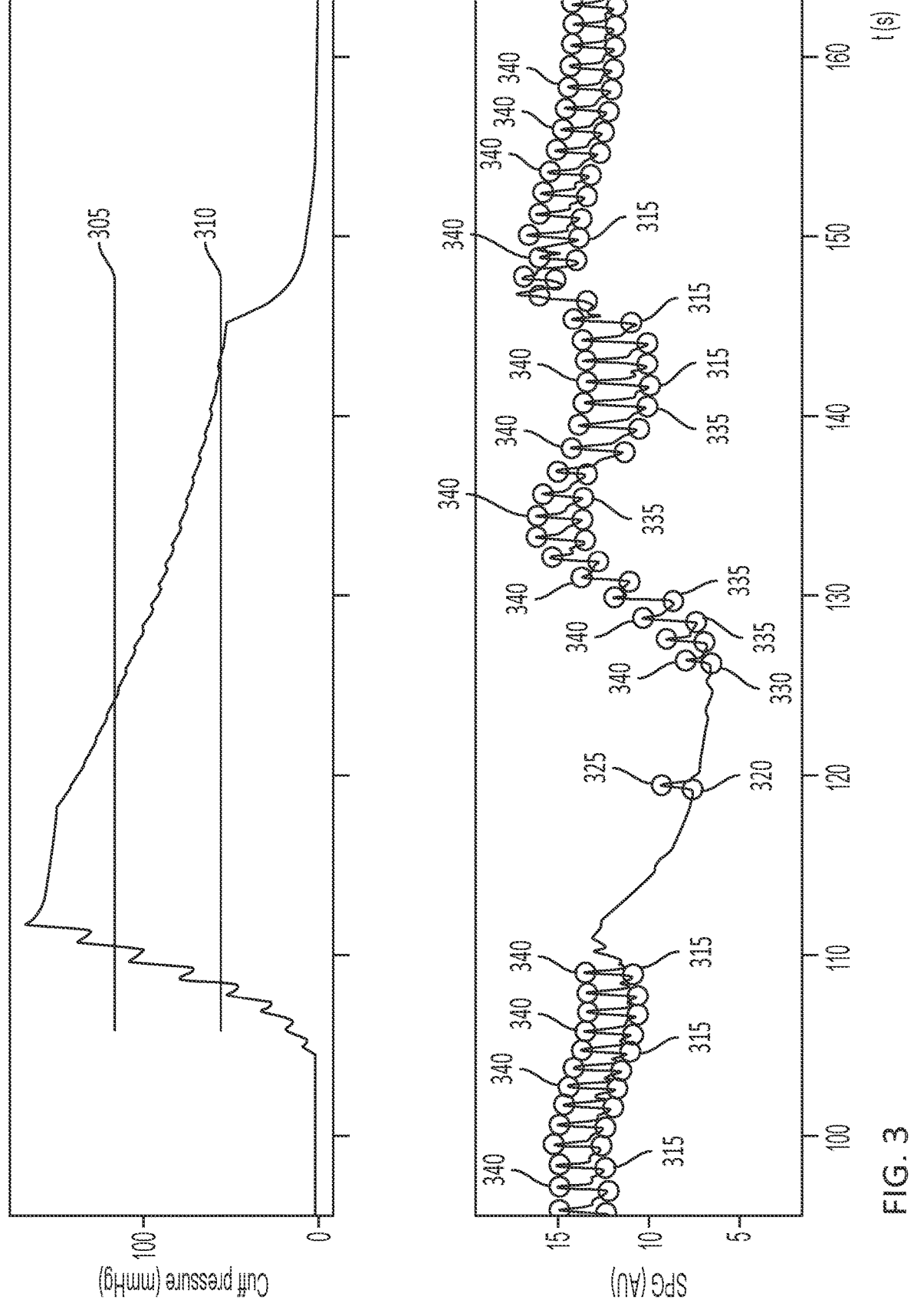
FIG. 3 is a graph of cuff pressure and a graph of blood flow velocity, according to an embodiment of the present disclosure.

FIG. 3 shows two graphs, a graph of cuff pressure (the upper graph of FIG. 3) and a graph of the blood flow velocity signal (the lower graph of FIG. 3). The upper graph shows the systolic pressure 305 and the diastolic pressure 310, determined using methods disclosed herein. The lower graph shows the onsets 315 of a plurality of pulses, in the blood flow velocity signal, before the cuff inflation and after the cuff deflation, the onset 320 and peak 325 of a peak due to noise, the onset 330 of a first detected pulse during deflation (which may be detected using one or more of the methods disclosed herein), the onsets 335 of each of a plurality of additional pulses during deflation from systolic pressure to diastolic pressure, and the peak 340 of a each of a plurality of pulses.

Figure 4:
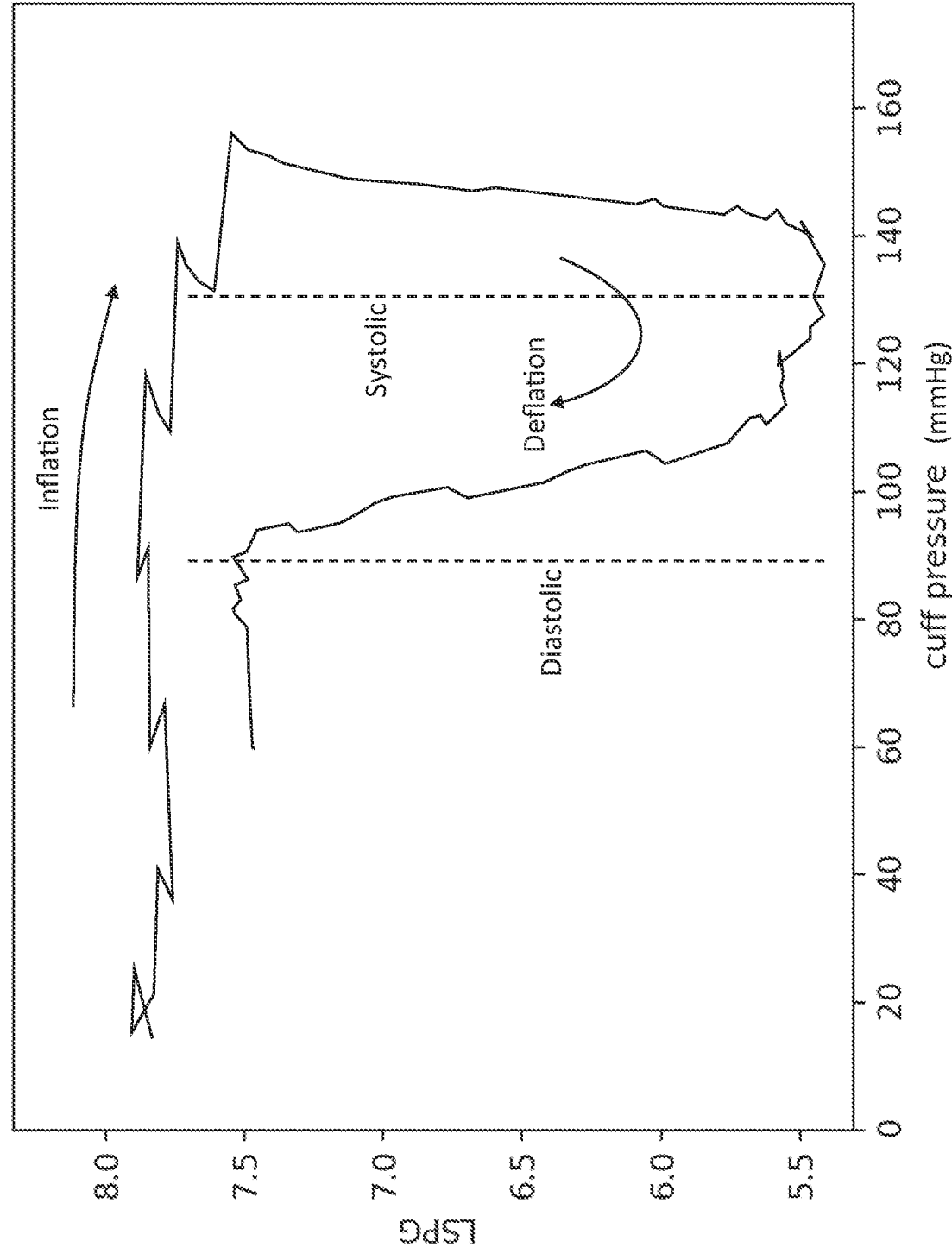
FIG. 4 is a graph of cuff pressure and low-frequency blood flow velocity, according to an embodiment of the present disclosure.

In some embodiments, a low-frequency speckleplethysmography method is used as a measure of blood flow to determine the systolic pressure, as illustrated in FIG. 4. FIG. 4 is a graph of a low-frequency (filtered) blood flow velocity (LSPG) signal graphed against the cuff pressure during inflation (the upper part of the graph) and deflation (the lower part of the graph). The low-frequency blood flow velocity signal may be obtained from the blood flow velocity (SPG) signal by low-pass filtering (e.g., with a corner frequency of 0.5 Hz) and the cuff pressure signal may also be processed by low-pass filtering (e.g., with a corner frequency of 0.15 Hz). In the method of FIG. 4, a minimum in the low-frequency blood flow velocity signal may be used as an estimate of (e.g., to determine) the systolic pressure as shown (with the systolic pressure being at the center of the minimum extending from 125 mmHg to 135 mm Hg). The minimum may be the point at which the low-frequency blood flow velocity signal first indicates, during deflation, an increase in blood flow. The diastolic pressure may also be estimated, as the cuff pressure during deflation at which the low frequency blood flow velocity ceases to increase. In some embodiments, the systolic pressure is calculated as a weighted sum of (i) a first value of the systolic blood pressure, determined using speckleplethysmography pulse detection; and (ii) a second value of the systolic blood pressure, determined using a low-frequency speckleplethysmography method.

Figure 5:
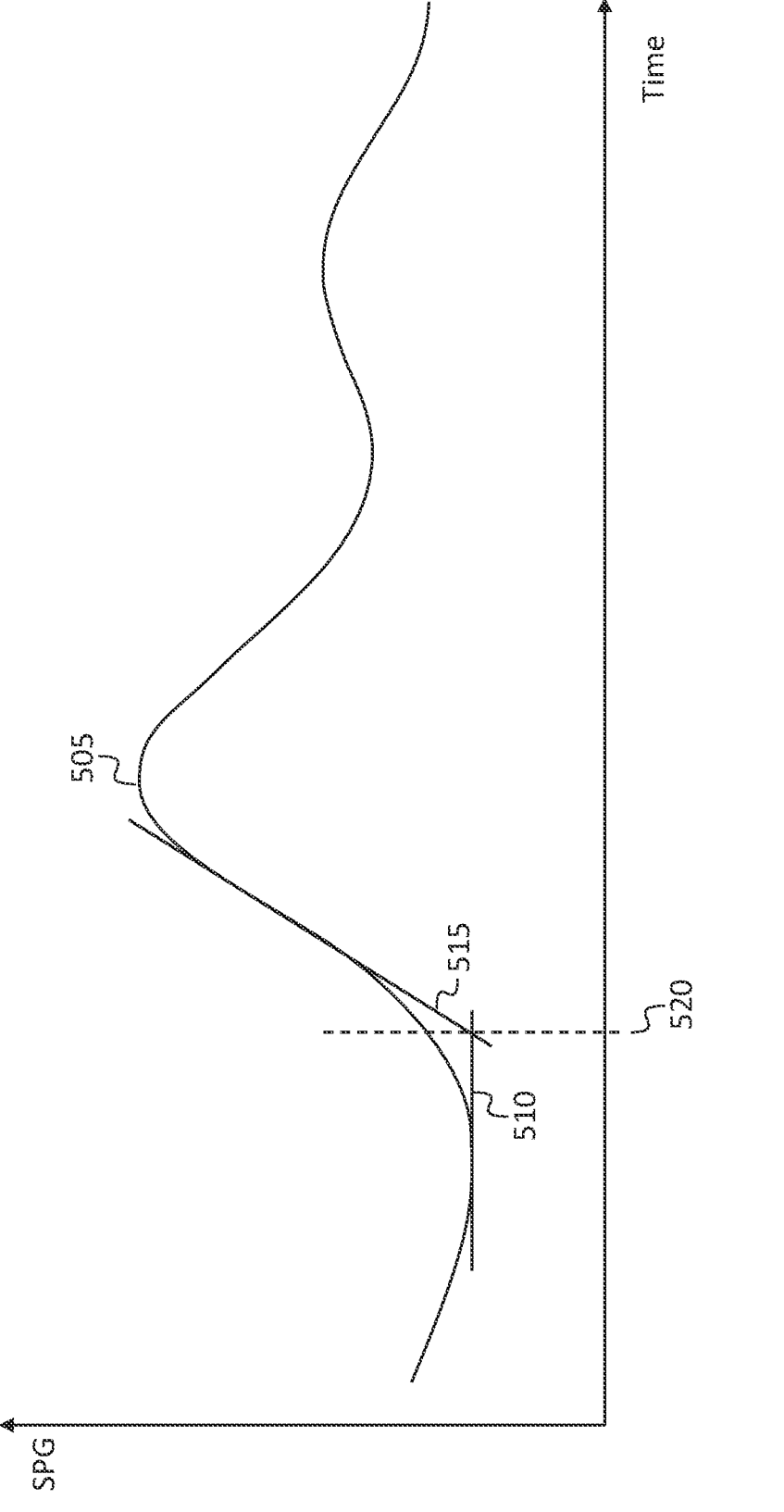
FIG. 5 is a graph of blood flow velocity, according to an embodiment of the present disclosure.

FIG. 5 illustrates a method for determining the onset of a pulse having a peak 505, in some embodiments. A first tangent 510 is a (horizontal) tangent to the blood flow velocity (SPG) signal at the minimum immediately preceding the peak 505, and a second tangent 515 is a tangent to the point at which the slope is greatest between the minimum and the peak 505. In the method of FIG. 5, the time corresponding to the intersection of the tangents 510, 515 is defined to be the onset of the pulse.

Figure 6:
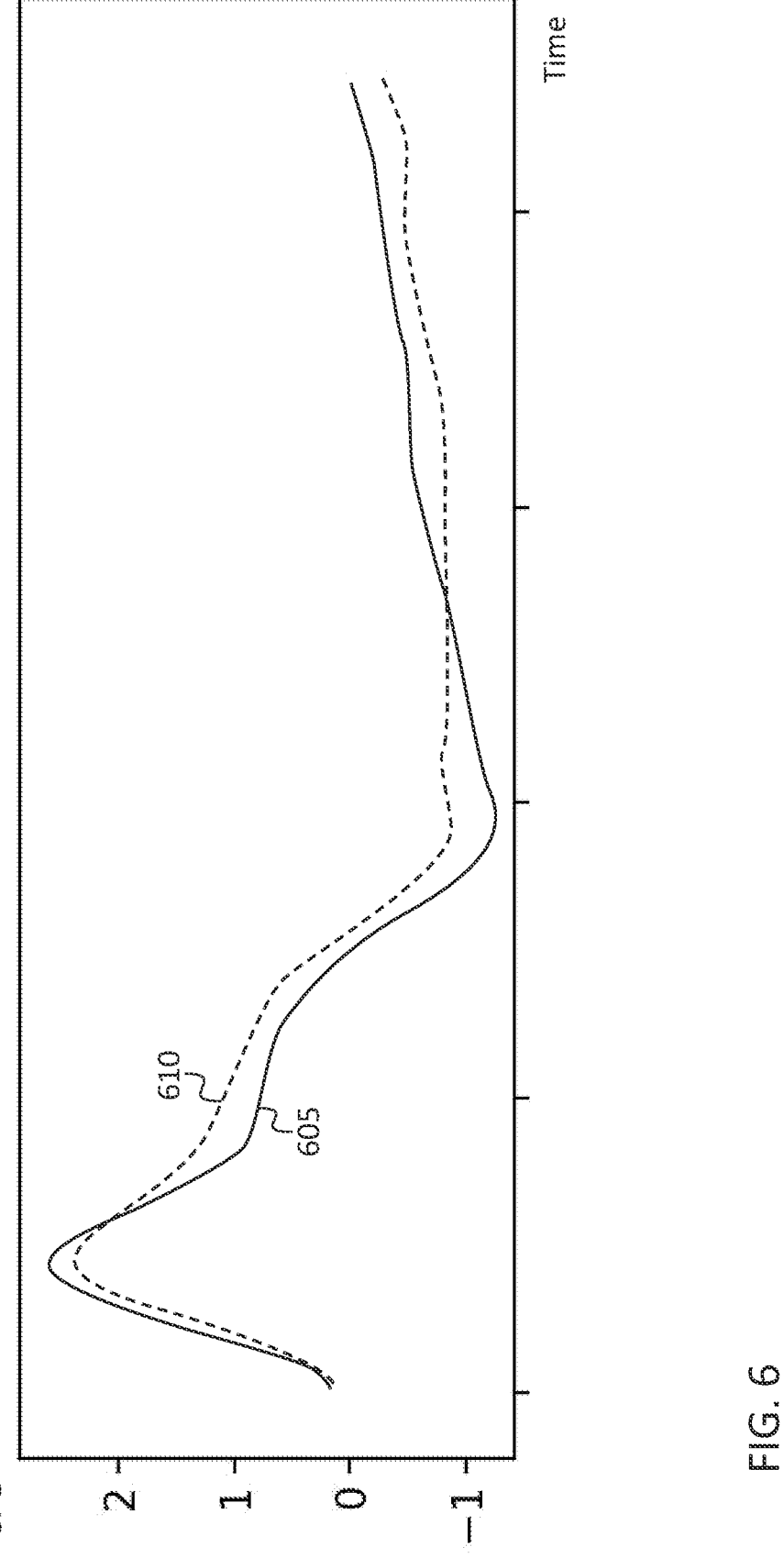
FIG. 6 is a graph of blood flow velocity and a graph of a template, according to an embodiment of the present disclosure.

Diastolic pressure may be measured using any, or any combination, of several different methods, including the method of FIG. 4 (discussed above). In one method, which may be referred to as "pulse template matching", template waveforms of the blood flow velocity during the cardiac cycle are obtained before cuff inflation and stored (or averaged and stored), and then used during cuff deflation to determine the diastolic pressure. During cuff deflation, after the cuff pressure initially drops below the systolic pressure, the blood flow velocity waveform may be distorted (relative to the pre-inflation waveform) because compression of the artery by the cuff impedes or stops blood flow during some or all of the cardiac cycle. As the cuff pressure continues to decrease, the waveform becomes more similar to the pre-inflation waveform. As such, each detected pulse (e.g., detected using the pulse detection methods discussed above) may be compared to one or more stored templates (e.g., to a template formed by averaging a plurality of pre-inflation waveforms) and a template-matching error (e.g., a discrepancy between the speckleplethysmography signal and the template waveform) may be calculated (e.g., by calculating the Euclidean distance between the candidate pulse and the template). FIG. 6 shows the waveform 605 of a detected pulse and the waveform of a template 610, in one example. If the pulse is the first pulse with a template matching error less than a threshold (e.g., a threshold between 0.05 and 0.3 of the peak-to-peak amplitude of the detected pulse or of the template) (and, in some embodiments, if the pulse also meets certain diastolic pulse requirements), the diastolic pressure may be determined to be the cuff pressure at the time the pulse was received. The diastolic pulse requirements may include a requirement that the cuff pressure at the time of the diastolic pulse is less than the mean arterial pressure.

In another method for determining diastolic pressure, referred to as "maximum amplitude detection", the cuff pressure at the time of the detected pulse with the greatest amplitude (e.g., peak to peak amplitude) in the blood flow velocity signal during cuff deflation is used as the diastolic pressure, as long as the cuff pressure at the time of said pulse is less than the mean arterial pressure. In some embodiments, the diastolic pressure is calculated as a weighted sum of values determined using different methods of the methods disclosed above, e.g., as a weighted sum of (i) a first value of the diastolic blood pressure determined using pulse template matching; and (ii) a second value of the diastolic blood pressure, determined using maximum amplitude detection.

Although some examples are disclosed herein including a pressure cuff and a speckleplethysmography sensor 125 on an arm of a subject, the invention is not limited to such embodiments and these components may be otherwise placed on the subject, e.g., on another limb (e.g., on a leg) or on another appendage (e.g., on a toe or on a finger, or on the tail of a vertebrate having a tail). The use of systems and methods disclosed herein is not limited to measurements on humans and these systems and methods may, for example, be used on other mammals or other vertebrates. Although some examples are disclosed herein including a method in which blood pressures are determined (e.g., estimated) while the cuff is being deflated, in other embodiments the cuff pressure may be otherwise varied, e.g., blood pressures may be estimated while the cuff is being inflated.

As used herein, "a portion of" something means "at least some of" the thing, and as such may mean less than all of, or all of, the thing. As such, "a portion of" a thing includes the entire thing as a special case, i.e., the entire thing is an example of a portion of the thing. As used herein, when a second quantity is "within Y" of a first quantity X, it means that the second quantity is at least X−Y and the second quantity is at most X+Y. As used herein, when a second number is "within Y %" of a first number, it means that the second number is at least $(1−Y/100)$ times the first number and the second number is at most $(1+Y/100)$ times the first number. As used herein, the word "or" is inclusive, so that, for example, "A or B" means any one of (i) A, (ii) B, and (iii) A and B.

Each of the terms "processing circuit" and "means for processing" is used herein to mean any combination of hardware, firmware, and software, employed to process data or digital signals. Processing circuit hardware may include, for example, application specific integrated circuits (ASICs), general purpose or special purpose central processing units (CPUs), digital signal processors (DSPs), graphics processing units (GPUs), and programmable logic devices such as field programmable gate arrays (FPGAs). In a processing circuit, as used herein, each function is performed either by hardware configured, i.e., hard-wired, to perform that function, or by more general-purpose hardware, such as a CPU, configured to execute instructions stored in a non-transitory storage medium. A processing circuit may be fabricated on a single printed circuit board (PCB) or distributed over several interconnected PCBs. A processing circuit may contain other processing circuits; for example, a processing circuit may include two processing circuits, an FPGA and a CPU, interconnected on a PCB.

As used herein, when a method (e.g., an adjustment) or a first quantity (e.g., a first variable) is referred to as being "based on" a second quantity (e.g., a second variable) it means that the second quantity is an input to the method or influences the first quantity, e.g., the second quantity may be an input (e.g., the only input, or one of several inputs) to a function that calculates the first quantity, or the first quantity may be equal to the second quantity, or the first quantity may be the same as (e.g., stored at the same location or locations in memory as) the second quantity.

The terminology used herein is for the purpose of describing particular embodiments only and is not intended to be limiting of the inventive concept. As used herein, the terms "substantially," "about," and similar terms are used as terms of approximation and not as terms of degree, and are intended to account for the inherent deviations in measured or calculated values that would be recognized by those of ordinary skill in the art.

Any numerical range recited herein is intended to include all sub-ranges of the same numerical precision subsumed within the recited range. For example, a range of "1.0 to 10.0" or "between 1.0 and 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Similarly, a range described as "within 35% of 10" is intended to include all subranges between (and including) the recited minimum value of 6.5 (i.e., $(1−35/100)$ times 10) and the recited maximum value of 13.5 (i.e., $(1+35/100)$ times 10), that is, having a minimum value equal to or greater than 6.5 and a maximum value equal to or less than 13.5, such as, for example, 7.4 to 10.6. Any maximum numerical limitation recited herein is intended to include all lower numerical limitations subsumed therein and any minimum numerical limitation recited in this specification is intended to include all higher numerical limitations subsumed therein.

Although exemplary embodiments of a system and method for measuring blood pressure have been specifically described and illustrated herein, many modifications and variations will be apparent to those skilled in the art. Accordingly, it is to be understood that a system and method for measuring blood pressure constructed according to principles of this disclosure may be embodied other than as specifically described herein. The invention is also defined in the following claims, and equivalents thereof.

What is claimed is:

1. A method, comprising:
measuring a first blood pressure,
the measuring of the first blood pressure comprising:
    varying a cuff pressure of a cuff on an appendage of a subject and coupled to a controller configured to control the cuff pressure;
    generating a speckleplethysmography signal from a speckleplethysmography sensor on the appendage and coupled to the controller, the speckleplethysmography sensor comprising a coherent light source, configured to illuminate tissue of the subject, and an image sensor configured to receive light from the tissue; and
    determining the first blood pressure based on the speckleplethysmography signal and based on the cuff pressure,
wherein:
    the first blood pressure is a systolic blood pressure, and
    the determining of the first blood pressure comprises:
        decreasing the cuff pressure; and
        determining the cuff pressure at a point in time, while the cuff pressure is decreasing, at which a measure of blood flow, based on the speckleplethysmography signal, indicates an increase in blood flow, and
    wherein the measure of blood flow is based on a method of pulse detection, comprising:
        calculating a measure of quality of a candidate pulse; and
        determining whether the candidate pulse is part of a sequence of pulses.

2. The method of claim 1, wherein the determining of whether the candidate pulse is part of a sequence of pulses comprises:
determining whether an amplitude of the candidate pulse is consistent with an amplitude trend within the sequence of pulses, and
determining whether a position in time of the candidate pulse is consistent with positions in time of the sequence of pulses.

3. The method of claim 1, wherein the speckleplethysmography signal is low-pass filtered, and the measure of blood flow is based on the low-pass filtered speckleplethysmography signal.

4. A method, comprising:
measuring a first blood pressure,
the measuring of the first blood pressure comprising:
    varying a cuff pressure of a cuff on an appendage of a subject and coupled to a controller configured to control the cuff pressure;
    generating a speckleplethysmography signal from a speckleplethysmography sensor on the appendage and coupled to the controller, the speckleplethys-
mography sensor comprising a coherent light source,
configured to illuminate tissue of the subject, and an
image sensor configured to receive light from the
tissue; and determining the first blood pressure based on the speck-
leplethysmography signal and based on the cuff
pressure, wherein:

the first blood pressure is a diastolic blood pressure, and
the determining of the first blood pressure comprises:
decreasing the cuff pressure; and
determining the cuff pressure at a point in time, while
the cuff pressure is decreasing, at which the speck-
leplethysmography signal has a maximum ampli-
tude.

5. A method, comprising:

measuring a first blood pressure, the measuring of the first blood pressure comprising:
varying a cuff pressure of a cuff on an appendage of a
subject and coupled to a controller configured to
control the cuff pressure;

generating a speckleplethysmography signal from a
speckleplethysmography sensor on the appendage
and coupled to the controller, the speckleplethys-
mography sensor comprising a coherent light source,
configured to illuminate tissue of the subject, and an
image sensor configured to receive light from the
tissue; and determining the first blood pressure based on the speck-
leplethysmography signal and based on the cuff
pressure, wherein:

the first blood pressure is a diastolic blood pressure, and
the determining of the first blood pressure comprises:
decreasing the cuff pressure; and
determining the cuff pressure at a point in time, while
the cuff pressure is decreasing, at which a discrep-
ancy between the speckleplethysmography signal
and a template waveform is less than a threshold.

6. A method, comprising:

measuring a first blood pressure, the measuring of the first blood pressure comprising:
varying a cuff pressure of a cuff on an appendage of a
subject and coupled to a controller configured to
control the cuff pressure;

generating a speckleplethysmography signal from a
speckleplethysmography sensor on the appendage
and coupled to the controller, the speckleplethys-
mography sensor comprising a coherent light source,
configured to illuminate tissue of the subject, and an
image sensor configured to receive light from the
tissue; and determining the first blood pressure based on the speck-
leplethysmography signal and based on the cuff
pressure, wherein:

the first blood pressure is a diastolic blood pressure, and
the determining of the first blood pressure comprises:
decreasing the cuff pressure; and
determining the cuff pressure at a point in time, while
the cuff pressure is decreasing, at which a low-
frequency speckleplethysmography signal ceases
to increase.

* * * * *